(12) United States Patent
Murphy et al.

(10) Patent No.: US 11,110,238 B2
(45) Date of Patent: *Sep. 7, 2021

(54) RESUSCITATOR DEVICE

(71) Applicant: Safeguard Medical Holdco, LLC, Harrisburg, NC (US)

(72) Inventors: Christopher Murphy, Vass, NC (US); Corey Russ, Fayetteville, NC (US)

(73) Assignee: Safeguard Medical Hodco, LLC, Harrisburg, NC (US)

( * ) Notice: Subject to any disclaimer, the term of this patent is extended or adjusted under 35 U.S.C. 154(b) by 456 days.

This patent is subject to a terminal disclaimer.

(21) Appl. No.: 15/948,804

(22) Filed: Apr. 9, 2018

(65) Prior Publication Data

US 2019/0046747 A1 Feb. 14, 2019

Related U.S. Application Data

(63) Continuation of application No. 14/324,739, filed on Jul. 7, 2014, now Pat. No. 9,937,310, which is a
(Continued)

(51) Int. Cl.
*A61M 16/08* (2006.01)
*A61M 16/00* (2006.01)
(Continued)

(52) U.S. Cl.
CPC .... *A61M 16/0084* (2014.02); *A61M 16/0075* (2013.01); *A61M 16/0078* (2013.01);
(Continued)

(58) Field of Classification Search
CPC ...... A61B 5/0002; A61B 5/093; A61M 16/00; A61M 16/0075; A61M 16/0078; A61M 16/0084; A61M 16/06; A61M 16/0875; A61M 16/1055; A61M 16/106; A61M 16/107; A61M 16/201; A61M 16/22; A61M 2016/0027; A61M 2205/581; A61M 2205/582; A61M 2205/584; A62B 7/10; G09B 23/28; G09B 23/288; G16H 40/63; Y10S 128/909; Y10S 128/91
See application file for complete search history.

(56) References Cited

U.S. PATENT DOCUMENTS 1,070,986 A  8/1913  Richter
1,359,312 A  11/1920 Bardwell
(Continued)

OTHER PUBLICATIONS

International Application No. PCT/US2013/023265, International Search Report dated Apr. 12, 2013, 2 pages.
(Continued)

*Primary Examiner* — Annette Dixon
(74) *Attorney, Agent, or Firm* — Corner Counsel, LLC

(57) ABSTRACT

A manually actuated, self-inflating bag valve mask provides users with a positive pressure ventilation device that reliably provides a proper tidal volume to the patient and controls the rate of ventilation of the patient. The bag valve mask is lightweight, compact, durable, and quickly deployable in the field. The device is preferably operable with one hand and can be configured for use in low-light environments.

17 Claims, 8 Drawing Sheets

Related U.S. Application Data continuation of application No. PCT/US2013/023265, filed on Jan. 25, 2013.

(60) Provisional application No. 61/591,800, filed on Jan. 27, 2012.

(51) Int. Cl.
  *A61M 16/06* (2006.01)
  *A61M 16/20* (2006.01)
  *A61M 16/10* (2006.01)

(52) U.S. Cl.
  CPC ........ *A61M 16/06* (2013.01); *A61M 16/0875* (2013.01); *A61M 16/201* (2014.02); *A61M 16/107* (2014.02); *A61M 2016/0027* (2013.01); *A61M 2205/581* (2013.01); *A61M 2205/582* (2013.01); *A61M 2205/584* (2013.01)

(56) References Cited

U.S. PATENT DOCUMENTS

| | | | | |
|---|---|---|---|---|
| 3,067,741 | A | 12/1962 | Croasdaile | |
| 3,575,167 | A * | 4/1971 | Michielsen | A62B 7/10 128/205.28 |
| 3,808,706 | A * | 5/1974 | Mosley | A61B 5/093 73/865.9 |
| 3,890,967 | A * | 6/1975 | Elam | A61M 16/0084 128/205.17 |
| 4,067,328 | A * | 1/1978 | Manley | A61M 16/00 128/202.27 |
| 4,349,015 | A | 9/1982 | Alferness | |
| 4,870,962 | A | 10/1989 | Sitnik | |
| 4,898,167 | A | 2/1990 | Pierce et al. | |
| 4,934,360 | A | 6/1990 | Heilbron et al. | |
| 5,313,938 | A | 5/1994 | Garfield et al. | |
| 5,345,929 | A * | 9/1994 | Jansson | A61M 16/0075 128/205.13 |
| 5,787,880 | A | 8/1998 | Swanson et al. | |
| 5,875,775 | A | 3/1999 | Nur | |
| 6,067,984 | A | 5/2000 | Piper | |
| 6,341,606 | B1 | 1/2002 | Bordewick et al. | |
| 6,851,428 | B2 | 2/2005 | Dennis | |
| 6,938,618 | B2 | 9/2005 | Lurie et al. | |
| 6,988,499 | B2 | 1/2006 | Holt et al. | |
| 7,055,520 | B2 | 6/2006 | Swisa | |
| 7,658,188 | B2 | 2/2010 | Halpern et al. | |
| 7,980,244 | B2 | 7/2011 | Boone et al. | |
| 9,937,310 | B2 * | 4/2018 | Murphy | A61M 16/201 |
| 2003/0178025 | A1 | 9/2003 | Holt et al. | |
| 2005/0150495 | A1 | 7/2005 | Rittner et al. | |
| 2006/0272644 | A1 | 12/2006 | Halpern | |
| 2009/0071480 | A1 | 3/2009 | Adams | |
| 2010/0263670 | A1 * | 10/2010 | Pearce | A61M 16/0075 128/205.14 |
| 2010/0285439 | A1 * | 11/2010 | Mestad | G09B 23/28 434/272 |

OTHER PUBLICATIONS

International Application No. PCT/US2013/023265, International Preliminary Report dated May 5, 2015, 7 pages.

* cited by examiner

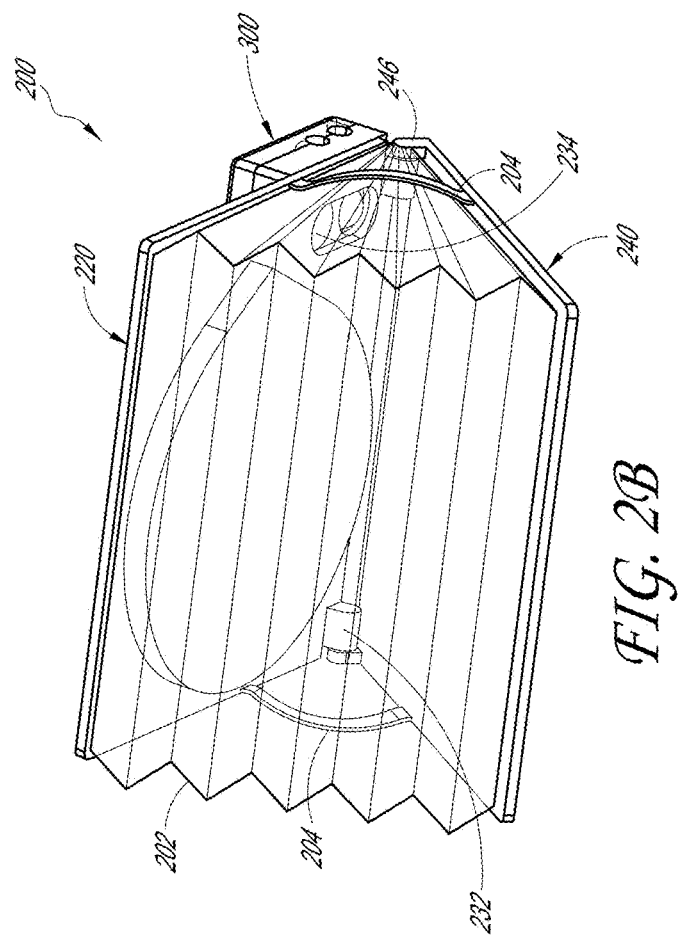
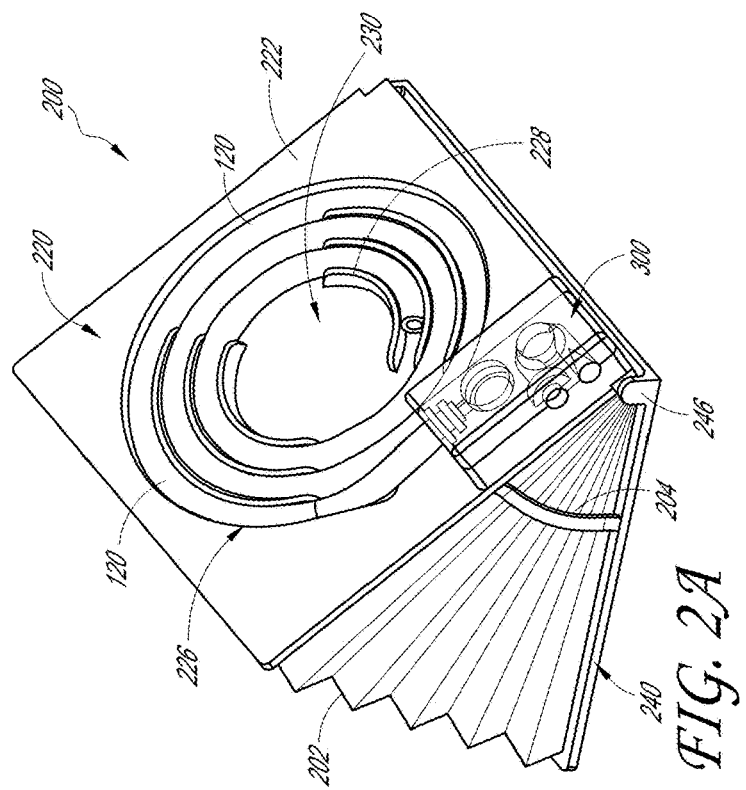

RESUSCITATOR DEVICE

INCORPORATION BY REFERENCE TO ANY PRIORITY APPLICATIONS

Any and all applications for which a foreign or domestic priority claim is identified in the Application Data Sheet as filed with the present application are incorporated by reference under 37 CFR 1.57 and made a part of this specification.

BACKGROUND

This application relates generally to resuscitator devices, and specifically to devices that provide positive pressure ventilation to assist the breathing of patients.

DESCRIPTION OF RELATED ART

A bag valve mask, often called a BVM, is a hand-held device used to provide positive pressure ventilation to patients who need assistance breathing. A BVM is used for affecting cardiopulmonary resuscitation, when breathing has been halted or impaired by immersion, trauma, or other suffocating circumstances. The device can be part of a resuscitation kit. The device is sometimes used in the operating room to ventilate an anaesthetized patient in the minutes before a mechanical ventilator is attached. The BVM device can be configured to ventilate ambient air or it can be attached to an oxygen source.

SUMMARY OF THE DISCLOSURE

In some embodiments, a manually actuated, self-inflating bag valve mask provides users with a positive pressure ventilation device that reliably provides a proper tidal volume to the patient and controls the rate of ventilation of the patient. In some embodiments, the bag valve mask can be lightweight, compact, durable, and quickly deployable in the field, and the device can be operable with one hand and can be configured for use in low-light environments.

Some BVM devices are prone to use in a way that induces underventilation or hyperventilation of the patient. Some BVM's recover to their normal shape slowly after compression. In emergency situations, this can precipitate anxiety in the operators as they find it very difficult to judge how much air has been forced into the patient's lungs. As a consequence of this uncertainly, the operators often over-compensate, which results in a tendency to over pressurize the lungs or hyperventilate the patient.

In some embodiments, resuscitator devices and components and subassemblies thereof are portable, manually actuated and designed for emergency use. In some embodiments, the resuscitator devices disclosed herein are especially suited for first responders, such as military medics and ambulance crews, and can provide the first responders with a patient ventilation device that provides the proper amount of air to the patient and controls the rate of ventilation of the patient. In some embodiments, the resuscitator devices are made of materials that allow the device to be sterilized using a plurality of different types of sterilization techniques.

The resuscitator device directs ambient gas inside it via a one-way valve when compressed by a rescuer. The gas is then delivered through a mask and into the patient's trachea, bronchus and into the lungs. In some embodiments, for normally sized adults, a bag valve mask may deliver between 500 and 800 milliliters of air to the patient's lungs, but if oxygen is provided through the tubing and if the patient's chest rises with each inhalation (indicating that adequate amounts of gas are reaching the lungs), 400 to 600 milliliters may still be adequate. In some embodiments, the resuscitator device can deliver gas (e.g., ambient air or oxygen or some combination thereof) to one or more patients at different volumes depending on one or more physiological characteristics of a patient, such as the patient's age, size, and/or lung capacity. In some embodiments, there are at least two different gas delivery volume settings for the resuscitator. For example, in a first setting, at least about 575 milliliters of gas and/or less than or equal to about 620 milliliters of gas can be delivered to an adult patient. For treating children, some embodiments can be configured to deliver at least about 300 and/or less than or equal to about 450 milliliters of gas at a second setting. In some embodiments, the duration of gas delivery can be adjusted depending on the patient's needs. For example, in a first setting or in a first procedure, a certain type of patient (e.g., an adult, a large person, and/or an a person with high lung capacity) can receive gas for a longer duration or there can be more time between dispensations of gas, and in a second setting or in a second procedure, a different type of patient (e.g., a child, a small person, and/or a person with small lung capacity) can receive gas for a shorter duration or there can be less time between dispensations of gas. For example, squeezing the bag about once every 5 to 6 seconds for an adult or about once every 3 to 4 seconds for an infant or child can provide an adequate respiratory rate (e.g., 12 respirations per minute in an adult and 20 per minute in a child or infant). In some embodiments, the resuscitator device can include structures and/or settings that permit, facilitate, or indicate different gas delivery duration times and/or different times between gas deliveries.

The mask portion of the resuscitator device is properly sealed around the patient's face ("mask seal"); otherwise, air can escape from the mask and is not pushed into the lungs. The term "seal" and related terms should not be interpreted to require a perfect seal in which no other gas ever leaks in or out, but rather a functional connection that is clinically effective in delivering the amount of a gas that is needed. Some methods of ventilation involve two rescuers: one rescuer holds the mask to the patient's face with both hands to ensure a mask seal, while the other squeezes the bag. However, as most ambulances have only two members of crew, the other crew member may be doing compressions in the case of CPR, or may be performing other interventions such as defibrillation or cannulation. In this or other cases, the resuscitator device can also be operated by a single rescuer who holds the mask to the patient's face with one hand (e.g., in the anesthetist's grip) and squeezes the bag with the other.

When using a resuscitator device, as with other methods of positive pressure ventilation, there is a risk of over-inflating the lungs. This can lead to pressure damage to the lungs themselves, and can also cause air to enter the stomach, causing gastric distension which can make it more difficult to inflate the lungs. Another consequence may be to cause the patient to vomit, which can cause additional airway problems beyond the original breathing difficulty. Some models of resuscitator devices (e.g., pediatric) can be fitted with a valve which prevents over-inflation, by venting the pressure when a pre-set pressure is reached. The "Sellick maneuver" (application of cricoid pressure) can be applied to reduce the risk of aspiration of gastric contents whenever possible until the trachea can be intubated or until there is no longer any need for positive pressure ventilation.

BRIEF DESCRIPTION OF THE DRAWINGS

Specific embodiments and modifications thereof will become apparent to those skilled in the art from the examples provided in the detailed description herein having reference to the figures that follow, of which:

FIG. 2A is a rear perspective view of a resuscitator bag in an open configuration, according to an embodiment in the present application.

FIG. 2B is a front perspective view of the resuscitator bag of FIG. 2A.

DETAILED DESCRIPTION OF SPECIFIC EMBODIMENTS

Examples of resuscitator devices for providing controlled positive pressure ventilation to patients are described herein. None of these examples should be understood to limit the inventions recited in the claims. None of the structures, steps, or other features disclosed herein are essential or indispensable; any can be omitted in some embodiments. Some of the resuscitator devices disclosed herein can be particularly advantageous for use in rugged and abusive combat or military environments, where quick and easy use of the device can be beneficial.

Resuscitator devices having desirable features and advantages will now be described with reference to the figures. Although the following description is provided in the context of an example of a resuscitator devices, the features of the present resuscitator devices can provide advantages in many other applications as well. For example, features described herein can be used in applications such as air inflators and water pumps.

In this application, the terms "upper," "lower," "top," and "bottom" are used as descriptive references of the components in the figures. However, these descriptions should not be construed as limiting the orientation or positions of the features described herein or as limiting the functionality of any of the components. For example, the upper plate of the resuscitator bag does not necessarily have to be above the lower plate to function properly. The resuscitator device would still function properly on its side, where the upper and lower plates are side-to-side, or upside-down where the lower plate is on top of the upper plate.

Figure 1:
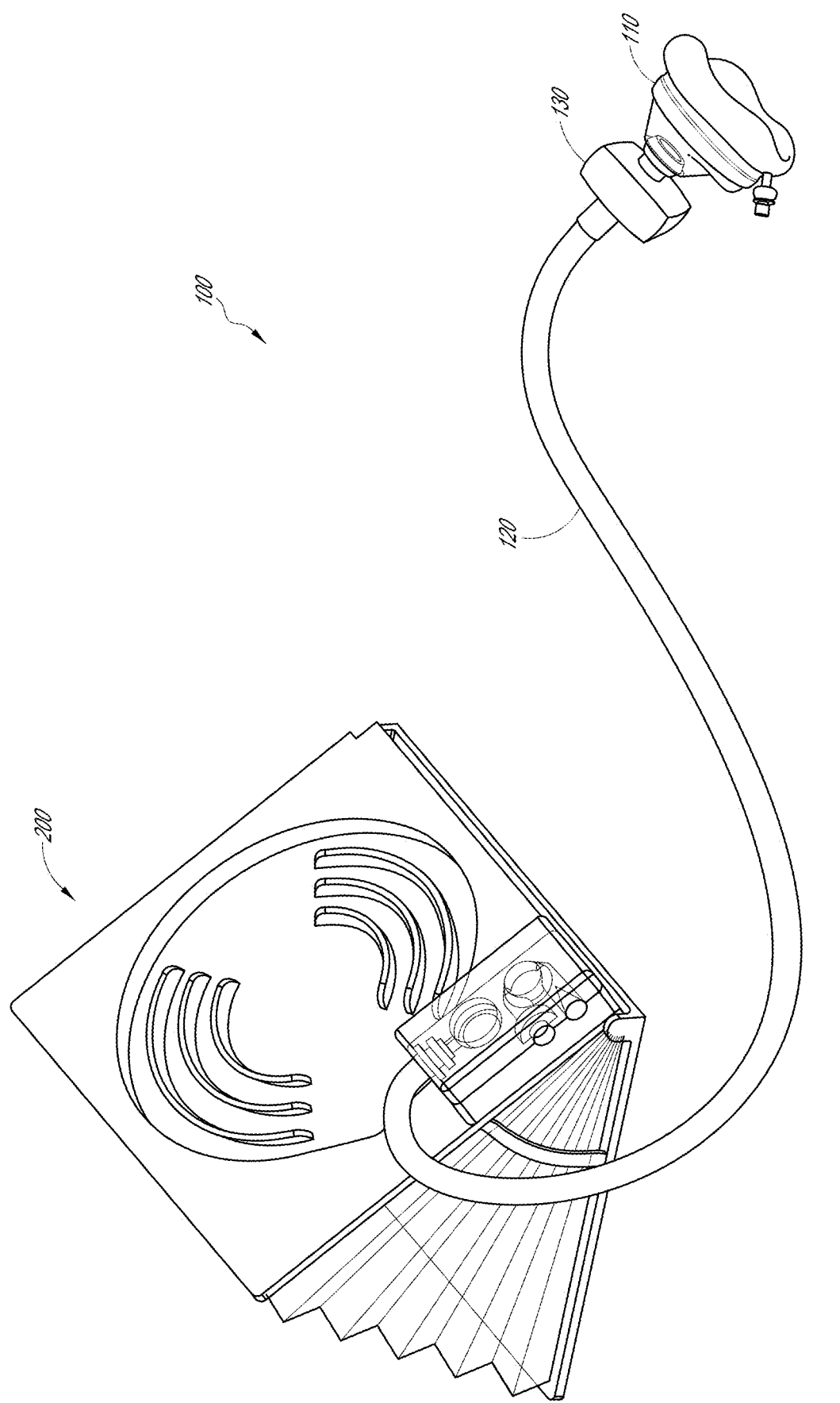
FIG. 1 is a perspective view of a bag valve mask according to an embodiment in the present application.

FIG. 1 illustrates an embodiment of a resuscitator device 100, also referred to as a bag valve mask, that includes a resuscitator bag 200 and a mask 110 coupled together with a hose, or tube 120. As will be explained in further detail below, the resuscitator bag 200 delivers proper tidal volumes and controlled positive pressure air ventilation through the tube 120 and out through the mask 110 into the patient.

Some resuscitator device devices can use a hand held bellows to produce pressurized air that is forced through an inhalation-exhalation valve, through a tube leading to a face mask and into the trachea and lungs of the patient. Upon exhalation, air exhausts in the reverse direction through the valve. Some resuscitator device devices can use a self-distending elastic bag that can be manually compressed.

Various types of mask 110 can be used. For example, the mask 110 can fit over the mouth and nose of the patient, creating a substantially air tight seal with the patient's face. When air is pushed through the mask 110, the air is directed into the patients' nose and/or mouth. The mask 110 can have a variety of sizes to fit infants, children and adults of varying sizes.

As illustrated in the embodiment of FIG. 1, the tube 120 can be connected at a first end to a valve assembly 300 (see FIG. 2A) on the resuscitator bag and connected at a second end to the mask 110. The tube 120 is preferably made of a medical grade material that is sterilized or sterilizable. Additionally, the tube 120 can be flexible for easy manipulation and durable enough to withstand use in harsh environments, such as by first responders.

In some embodiments, the resuscitator device 100 can include a filter 130 disposed between the resuscitator bag 200 and the mask 110. In the illustrated embodiment, the filter 130 is interposed between the second end of the tube 120 and the mask 110. The filter 130 can inhibit contamination from entering the resuscitator bag 200 and valve assembly 300, such as by emesis from the patient. The filter 130 can be particularly useful for reusable bag valve masks to maintain the sterility and cleanliness of the device. Even for disposable resuscitator devices, the filter 130 can help prevent contamination from causing the valve assembly 300 to malfunction or clogging the tube 120.

FIGS. 2A-B illustrate a resuscitator bag 200 having an upper plate 220, a lower plate 240, a bellows 202, springs 204 and a valve assembly 300. In the illustrated embodiment, the upper plate 220 and lower plate 240 are pivotally coupled together by hinges along an edge and the bellows 202 is disposed between the two plates 220, 240. For illustration purposes, the bellows 202 is shown as transparent in the figures; however, the bellows 202 can be made of non-transparent materials. The valve assembly 300 is attached to the upper plate 220 and is in fluid communication with the interior chamber of the bellows 202. The tube 120 can be connected to the valve assembly 300 and is in fluid communication with the interior chamber of the bellows 202. In the illustrated embodiment, the upper plate 220 includes a tube holder 226 with ridges 228 where the tube 120 can be wound or secured during storage and transport.

The several components of the resuscitator bag 200 in the illustrated embodiments will now be discussed in further detail. Although the embodiments herein are described as including the several components, the scope of the described device should not be limited by the particular embodiments described herein. Some embodiments may include a particular component, while other embodiments may not include the particular component, or be substituted with other similarly functioning components, and still fall within the scope of the present application.

Upper Plate

Figure 2C:
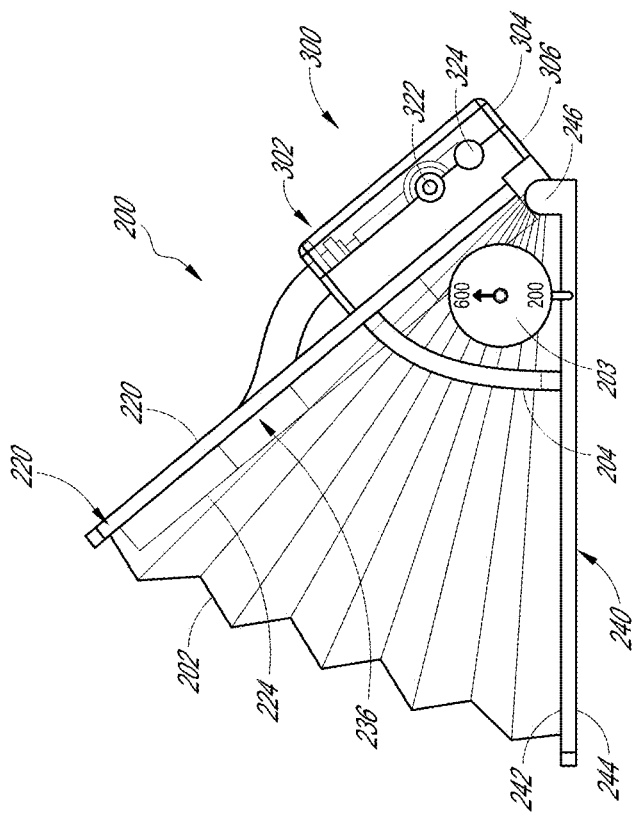
FIG. 2C is a left side elevation view of the resuscitator bag of FIG. 2A.
Figure 2D:
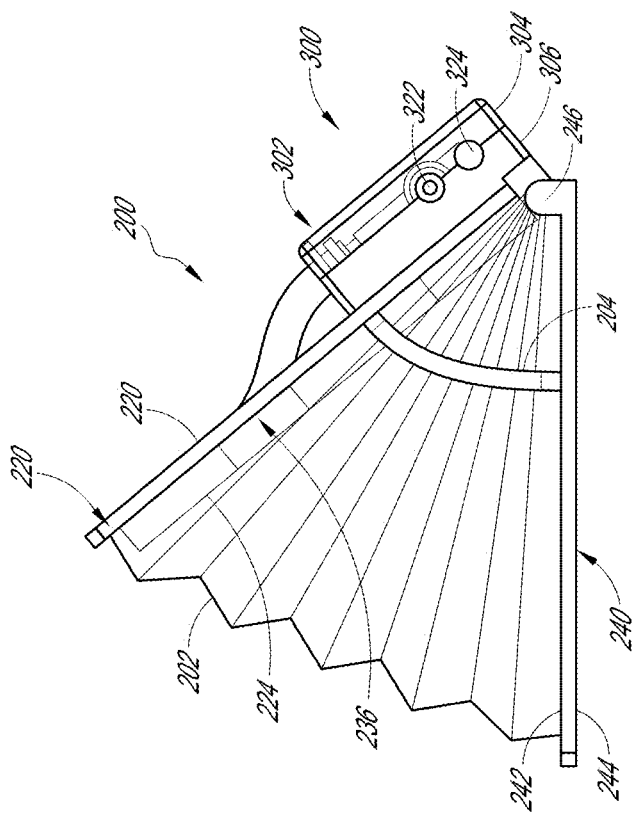
FIG. 2D is a left side elevation view of the resuscitator bag of FIG. 2A with a dial according to an embodiment in the present application.
Figure 3B:
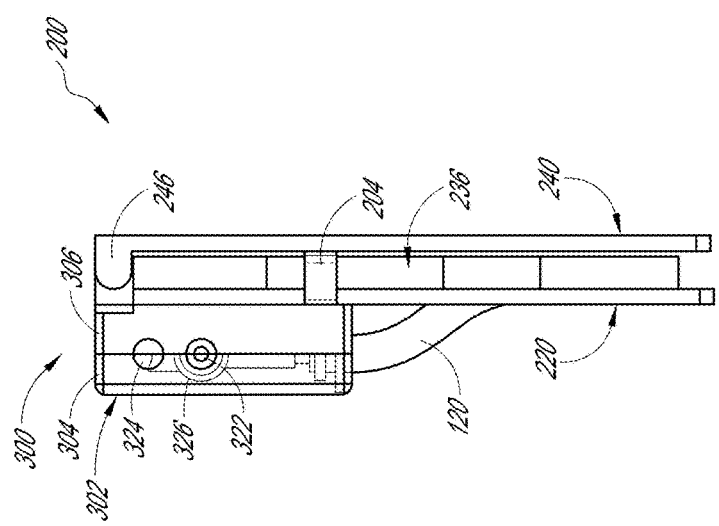
FIG. 3B is a side elevation view of the resuscitator bag of FIG. 3A.
Figure 3A:
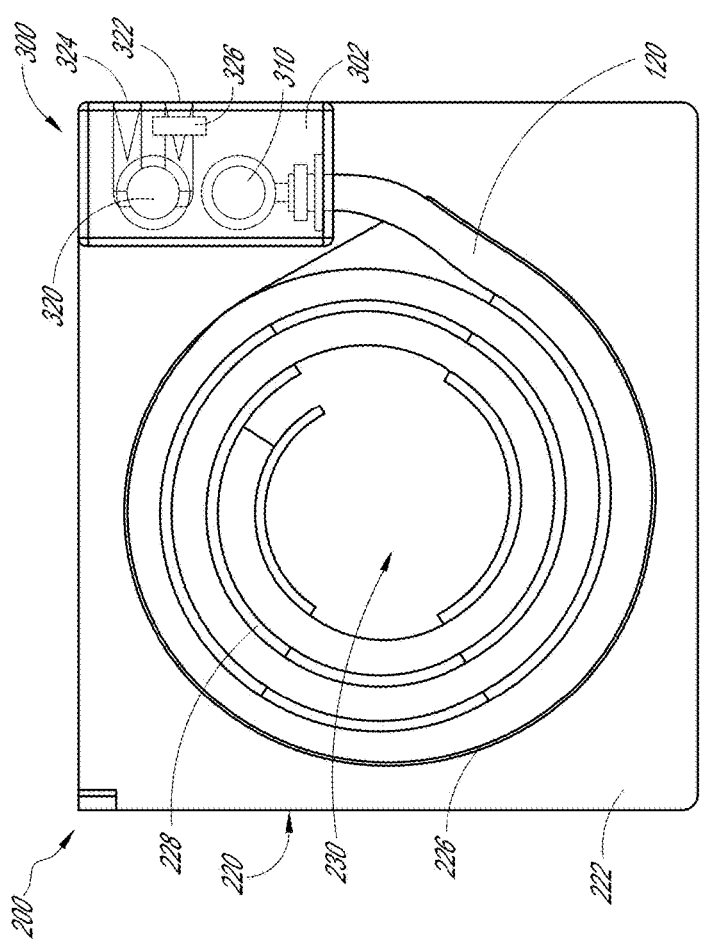
FIG. 3A is a top plan view of the resuscitator bag of FIG. 2A in a closed configuration.
Figure 3C:
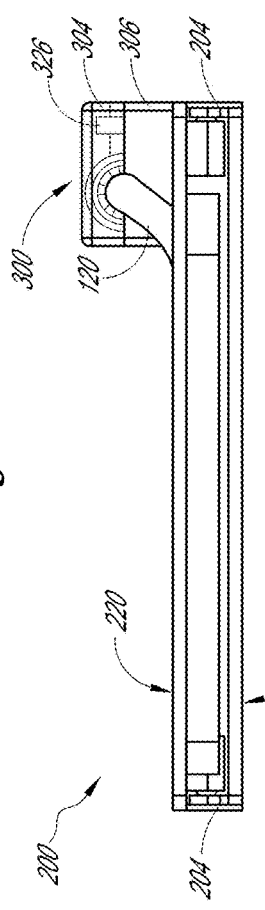
FIG. 3C is a front elevation view of the resuscitator bag of FIG. 3A.

With reference to FIGS. 2A-3C, the upper plate 220 can include a top surface 222 and a bottom surface 224. The upper plate 220 can be a generally wide component of small thickness. For example, in some embodiments, the upper plate 220 can be at least approximately 3 inches and/or less than or equal to approximately 8 inches in length. Further, the upper plate 220 can be at least approximately 4 inches and/or less than or equal to approximately 8 inches in width. In some embodiments, the thickness of the upper plate 220 can range from at least approximately 1/16 inches and/or less than or equal to approximately 1/2 inch. FIGS. 2A-C illustrate various views of the resuscitator bag 200 in an open configuration. FIGS. 3A-C illustrate various views of the resuscitator bag 200 in a closed configuration.

The upper plate 220 is preferably made of a lightweight, yet rigid material. For example, in some embodiments, the upper plate 220 can be made of a lightweight aluminum alloy and in other embodiments, the upper plate 220 can be made of a rigid plastic such as polycarbonate. The lightweight characteristic of the material can help reduce the load that first responders, such as battlefield medics, have to carry in the field. The rigidity of the material is helpful for providing support to the plates for compressing the bellows 202. The upper plate 220 material is also preferably made of a durable material that resists breaking, tearing and cracking. In some embodiments, the upper plate 220 material is transparent so that the interior of the resuscitator bag 200 can be inspected for debris and contamination. Some materials that can be used for the upper plate 220 include, but are not limited to, polyurethane, aluminum alloys, polycarbonate, polyethylene, carbon fiber and polycarbonates.

In some embodiments, the upper plate 220 can have at least one through-hole 234 that extends from the top surface 222 to the bottom surface 224. The hole 234 can allow air or other fluid to pass through the upper plate 220. In the illustrated embodiment, the upper plate 220 has two holes 234 that fluidly connect the interior of the bellows 202 with the valve assembly 300. In other embodiments, instead of a round hole through the upper plate 220, the resuscitator bag 200 can have a passageway or tube that extends between the upper plate 220 and lower plate 240 to connect the bellows 202 with the valve assembly.

The upper plate 220 can include a tube holder 226 that can be used to secure the tube 120 to the resuscitator bag 200 for storage and transport. In the illustrated embodiment, the tube holder 226 is a cavity on the top surface 222 of the upper plate 220 which is configured to receive the tube 120. The illustrated tube holder 226 includes ridges 228 for winding and guiding the tube in the tube holder 226. In some embodiments, the ridges 228 can be configured to provide a tight, secure fit for the tube 120, such as by providing spacing between ridges that is less than the outer diameter of the tube 120 to form an interference fit. The ridges 228 can advantageously provide a textured surface for better gripping of the resuscitator bag 200, especially when the tube 120 is detached from the tube holder 226.

In some embodiments, the center area of the tube holder 226 can include a mask holder 230. The mask holder 230 can provide an area to place the mask during storage and transport. The mask holder 230 can include features, such as the ridges described for the tube holder 226, which can hold or secure the mask to the resuscitator bag. In some embodiments, the securing features can include hooks, straps, pockets, or any of a plurality of different types of securing features. In some embodiments, the mask can be stored in the mask holder 230 while still connected to the tube 120.

The bottom surface 224 of the upper plate 220 can include a protrusion 236, which is formed by the cavity on the top surface 222 of the tube holder 226. When the upper plate 220 is closed onto the lower plate 240, the protrusion 236 can abut or be adjacent the top surface 242 of the lower plate 240, minimizing the space between the two plates 220, 240. This advantageously allows an efficient and reliable evacuation of the air in the bellows 202 when the resuscitator bag 200 is closed, which is helpful for repeatable ventilation of the patient.

Along an edge of the upper plate 220 can be one or more upper plate hinges 232. In the illustrated embodiment, the upper plate 220 includes two hinges 232 at the ends of an edge of the upper plate 220. In other embodiments, the hinge can extend along the entire length of the edge. In some embodiments, the hinges can be positioned in the middle or any other position along the edge. The upper plate hinges 232 can couple with lower plate hinges 246 on the lower plate 240 to form a pivoting coupling.

In some embodiments, the pivoting coupling can be created by a pin on the lower plate hinges 246 that is inserted into a cavity in the upper plate hinges 232, or vice-versa. The hinges can be configured for quick and easy assembly and disassembly. For example, the upper plate hinges 232 can include a slot which can accept the pin on the lower plate hinges 246. The slot and pin combination can allow the upper plate 220 and lower plate 240 to be assembled by bringing the plates together laterally at an angle of approximately 180° until the pin is inserted into the slot. The pin and slot can be configured so that when the plates are folded over, the hinges are locked together. The pin can be held in the slot through an interference fit, locks, or any of a plurality of different types of securing devices.

In other embodiments, the upper plate 220 and lower plate 240 can be attached through any of a plurality of different types of pivoting couplings. Some non-limiting examples can include straps or rings that extend through holes along the edges of the plates. Another example can include adhesive tape that adheres along the edges of the plates to couple the plate together. In some embodiments, the upper plate 220 and lower plate 240 can be an integral piece that is folded over to form the pivot, such as along a perforation or seam.

Lower Plate

The lower plate 240 can be a generally wide component of small thickness. For example, in some embodiments, the lower plate 240 can be at least approximately 4 inches and/or less than or equal to approximately 8 inches in length. Further, the lower plate 240 can be at least approximately 3 inches and/or less than or equal to approximately 8 inches in width. The thickness of the lower plate 240 can range from at least approximately 1/16 inches and/or less than or equal to approximately 1/2 inch. In the illustrated embodiment, the lower plate 240 is a flat component with two hinges 246 along an edge of the plate 240 that pivotally couple with the hinges 232 on the upper plate 220.

Similar to the upper plate 220, the lower plate 240 is preferably made of a lightweight, yet rigid material. For example, in some embodiments, the lower plate 240 can be made of a lightweight aluminum alloy and in other embodiments, the lower plate 240 can be made of a rigid plastic such as polycarbonate. As explained above, the lightweight characteristic of the material can help reduce the load that first responders have to carry in the field. The rigidity of the material is helpful for providing support to the plates for compressing the bellows 202. The lower plate 240 material is also preferably made of a durable material that resists breaking, tearing and cracking. In some embodiments, the lower plate 240 material is transparent so that the interior of the resuscitator bag 200 can be inspected for debris and contamination. Some materials that can be used for the lower plate 240 include, but are not limited to, polyurethane, aluminum alloys, polycarbonate, polyethylene, carbon fiber and polycarbonates.

Bellows

As illustrated in FIGS. 2A-2D, the bellows 202 can be an accordion-like structure that is disposed between the upper plate 220 and lower plate 240. The bellows 202 is an air chamber for holding and releasing air to the patient. The bellows 202 is preferably substantially impermeable to air and liquids to prevent leaking of air from the bellows 202 and also to prevent contamination of the air inside the bellows 202 from the environment. In some embodiments, the bellows 202 has a volume of at least approximately 100 milliliters and/or less than or equal to approximately 800 milliliters. In some embodiments, the bellows 202 has a volume of at least approximately 300 milliliters and/or less than or equal to approximately 400 milliliters.

In some embodiments, the bellows 202 can be made of a plastic material, such as polycarbonate or polyethylene, with a plurality of creases that allow the bellows 202 to fold or collapse. In some embodiments, the plastic can be flexible and can collapse without the need for preexisting creases in the material. In other embodiments, the bellows 202 can be made of a fabric-like material that is substantially impermeable to air. For example, the bellows 202 can be made of leather or fabric that is treated to make it airtight, such as with wax. In other embodiments, the bellows 202 can be made of a combination of materials that are layered together, such as for example fabric lined with a metallic foil. In some embodiments, the bellows 202 is at least partially made of a transparent material so that the air chamber can be inspected for contaminants.

In some embodiments, the bellows 202 can be attached to the upper plate 220 and/or lower plate 240 to form a chamber between the plates. For example, the bellows 202 can be sealed along the perimeter on the bottom surface 224 of the upper plate. Also, the bellows can be sealed along the perimeter on the top surface 242 of the lower plate 240. In this example, the air chamber would be enclosed by the upper plate 220 on the top side, the lower plate 240 on the bottom side and the bellows 202 in the middle portion. The seal between the bellows 202 and the upper plate 220 and lower plate 240 can form an airtight seal, such as with adhesives, welding, or gasket connection.

In some embodiments, the bellows 202 can be self-enclosed to create an air chamber surrounded by the bellows material. This bladder-type bellows is advantageous because, the bellows 202 do not have to form an airtight seal with the upper plate 220 and lower plate 240 to form a chamber. The bladder-type bellows can still be adhered to or welded to the upper plate 220 or lower plate 240 to secure the bellows 202 to the resuscitator bag 200. In some embodiments, the bellows 202 can be attached with straps, hooks, or other releasable attaching methods so that the bellows 202 can be replaced or repaired. In some embodiments, a tube can extend from the bellows and can be connected to the valve assembly 300 such that the valve assembly 300 is in fluid communication with the air chamber. The tube can be connected to the valve assembly 300 through the hole 234 in the upper plate. In some embodiments, the bellows 202 can have a cutout that is sealed around the hole 234 in the upper plate 220 to create fluid communication between the air chamber and the valve assembly 300.

In some embodiments, the bellows 202 can be biased in the open or expanded configuration. For example, the bellows material itself can create a bias in the expanded configuration. In some embodiments (e.g., those with folded plastic), the bellows can have a spring force that biases the plastic into the unfolded configuration. In some embodiments, a restoring element, such as a resilient component or springs, can be integrated into the material of the bellows 202, or the restoring element can be placed in the air chamber of the bellows 202 to bias the bellows 202 in the expanded configuration. In some embodiments, the bellows 202 can contain one or more support structures that attach to the bellows 202 wall and that can be oriented generally parallel to the upper plate 220 and lower plate 240. In some embodiments, the one or more support structures can be made of metallic wire or can otherwise have an elongate, narrow, wire-like form. These support structures can be configured to form a closed loop that generally follows the perimeter of the bellows wall. The support structures can be beneficial in assisting in opening the resuscitator device as well as in maintaining the outer shape of the bellows within a certain flexing range during opening and closing, thereby maintaining a generally uniform tidal volume within the bellows and facilitating a generally predictable and repeatable opening and closing process. The support structures can help prevent the material that makes up the bellows from catching on part of the resuscitator device (such as either or both of the corners of the upper or lower plates) when it is being opened and closed.

In some embodiments a volume limiter, variable actuator, or controller, such as a clip, a dial, or a slider can be used to change a functional characteristic of the bellows, such as the maximum volume delivered when compressed, or the maximum tidal volume of the bellows 202 in its open or expanded configuration. For example, with no restrictions, the bellows 202 can have a tidal volume of a first value (e.g., about 800 milliliters in some embodiments), but an actuator can be used to restrict the ability of the bellows to fully expand and therefore stop expansion when the bellows 202 has reached a lower tidal volume value (e.g., about 400 milliliters). In some embodiments, an actuator can be used to restrict further compression of the upper plate 220 and/or lower plate 240 once they have been compressed to a set point having allowed the bellows 202 to deliver a desired tidal volume of air (e.g., about 400 milliliters). In some embodiments, there can be a plurality of settings and the settings can correspond to desired settings for adults and/or for children or for persons of different sizes and/or weights.

As illustrated in FIG. 2D, in some embodiments, the actuator can be a dial 203 attached to the side of the upper plate 220 and/or lower plate 240. When the dial 203 is set to a setting different from the maximum volume of the bellows 202, a lever or other adjustment structure can engage the upper plate 220 and/or lower plate 240 to restrict further expansion and maintain a maximum tidal volume corresponding to the setting on the dial 203. In some embodiments, the actuator can be attached to or comprise the restoring element to control the amount of restoring force or the distance over which the restoring force is applied. Being able to adjust the tidal volume can be helpful in the prevention of hyperventilation and over-inflation of the lungs in smaller patients such as children. In some embodiments, the dial 203 has a bias that urges the setting on the dial 203 toward a desired setting. For example, in many instances, it will be desirable to have a standard adult tidal volume such as about 600 milliliters as a default setting. The dial 203 would then have a bias that urges the dial 203 to the 600 milliliter setting. The tidal volume could be adjusted to another value, for example about 200 milliliters for a child, by moving the dial 203 with sufficient force to overcome the bias. In some embodiments there can be a plurality of settings on the dial 203, such as between about 300 milliliters and about 800 milliliters.

Figure 5A:
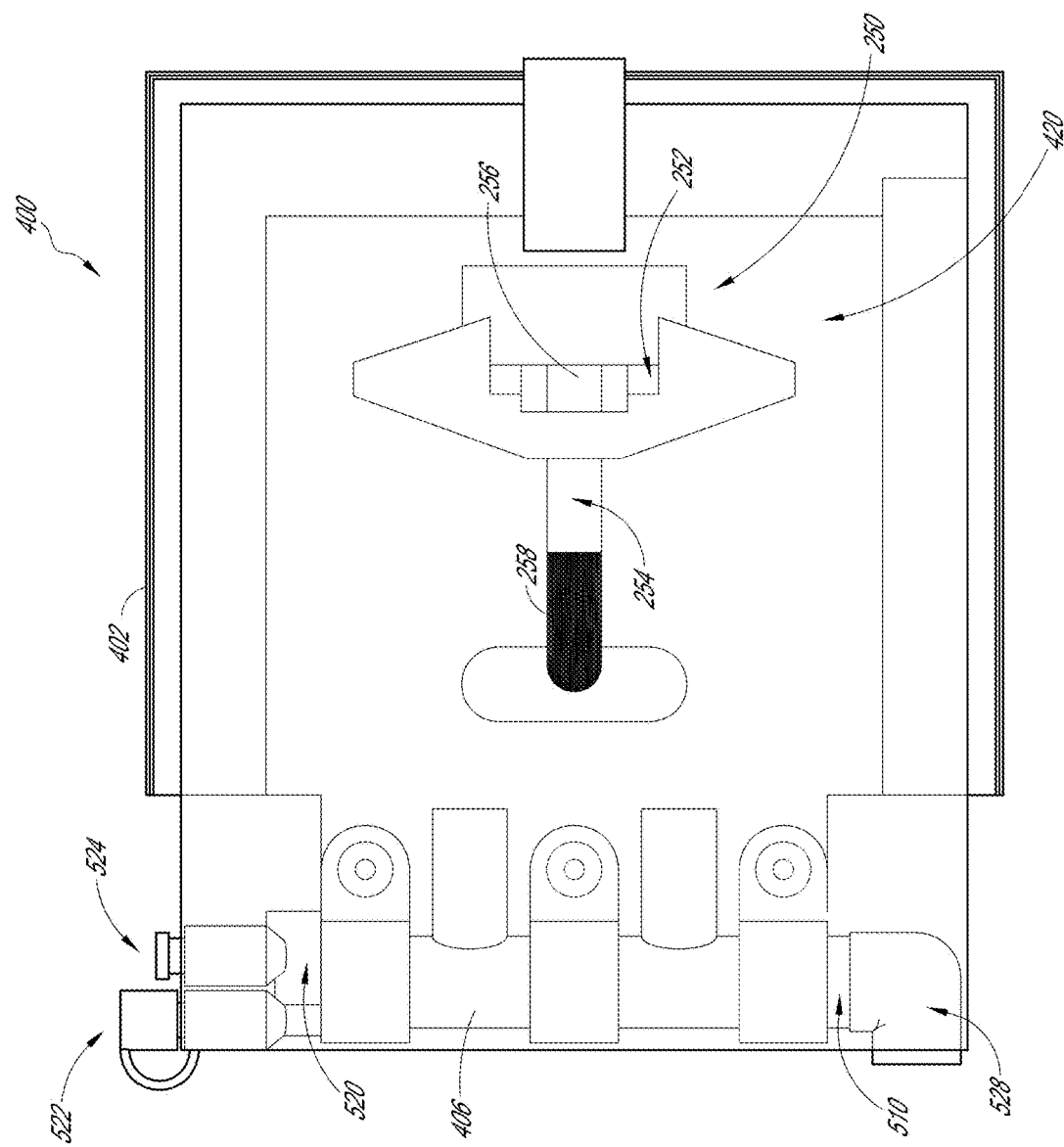
FIG. 5A is a top plan view of a resuscitator bag in a closed configuration, according to another embodiment in the present application.
Figure 5B:
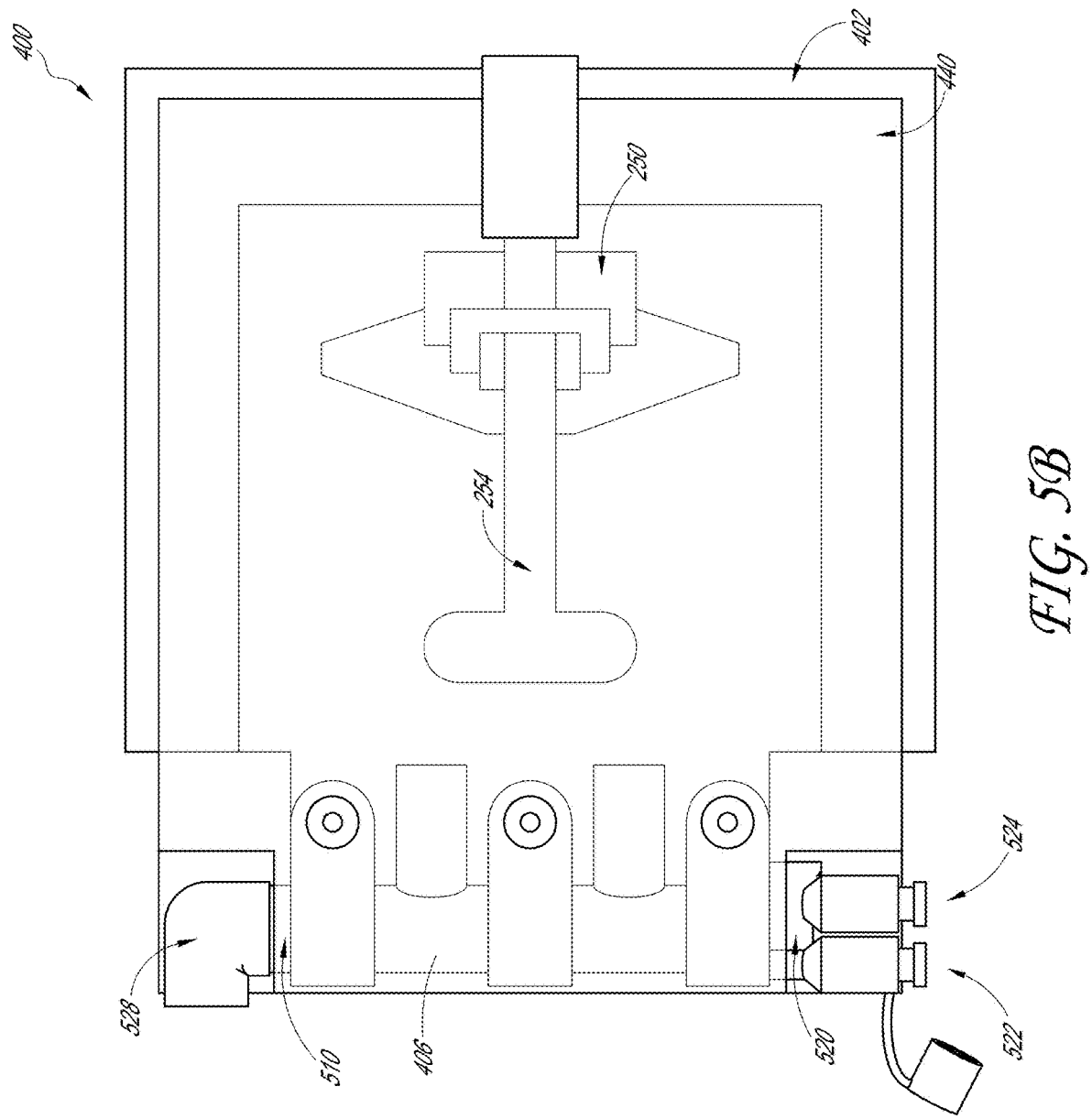
FIG. 5B is bottom plan view of the resuscitator bag of FIG. 5A.
Figure 6:
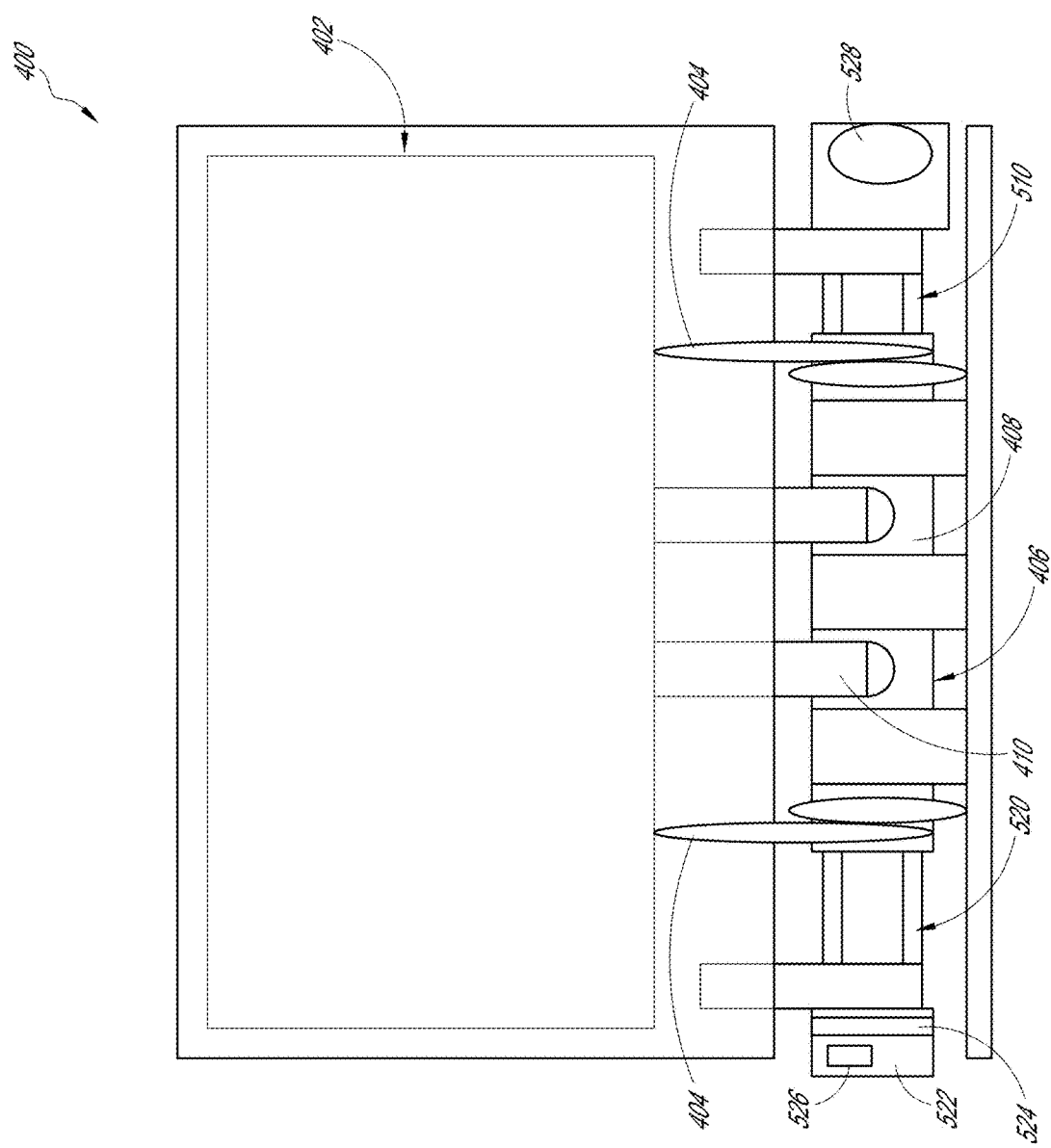
FIG. 6 is a top plan schematic view of the resuscitator bag of FIG. 5A.

In some embodiments, the actuator can be a switch or other control structure that is functionally linked to central flow line 406 which is illustrated in FIGS. 5A-B and 6. The switch can be set to a plurality of positions. For example, a first position can correspond to a first volume of air in the bellows 402 (e.g., about 600 milliliters). In this setting, the actuator allows the upper plate 420 and lower plate 440 to fully pivot away from each other which enables the bellows 402 to fully expand. When the switch is moved to a second position corresponding to a second volume of air (e.g., about 400 milliliters), the actuator moves to create a mechanical restriction on the movement of the upper plate 420 and lower plate 440 such that these plates are stopped at an earlier point from pivoting further away from each other once they are positioned to correspond to the lower tidal volume setting in the bellows 402. The maximum angle formed between the plates can be smaller in the second position than in the first position. In some embodiments, the switch can have more than two positions to correspond to multiple body types and/or tidal volumes.

In some embodiments, the actuator can be a clip that attaches to the upper plate 220 and lower plate 240. When the clip is attached to both plates, it prevents the bellows 202 from expanding and thus restricts the tidal volume to a desired amount determined by the length of the clips. In some embodiments there can be a plurality of clips that can be attached depending on the size of the patient.

Valve Assembly

Figure 4:
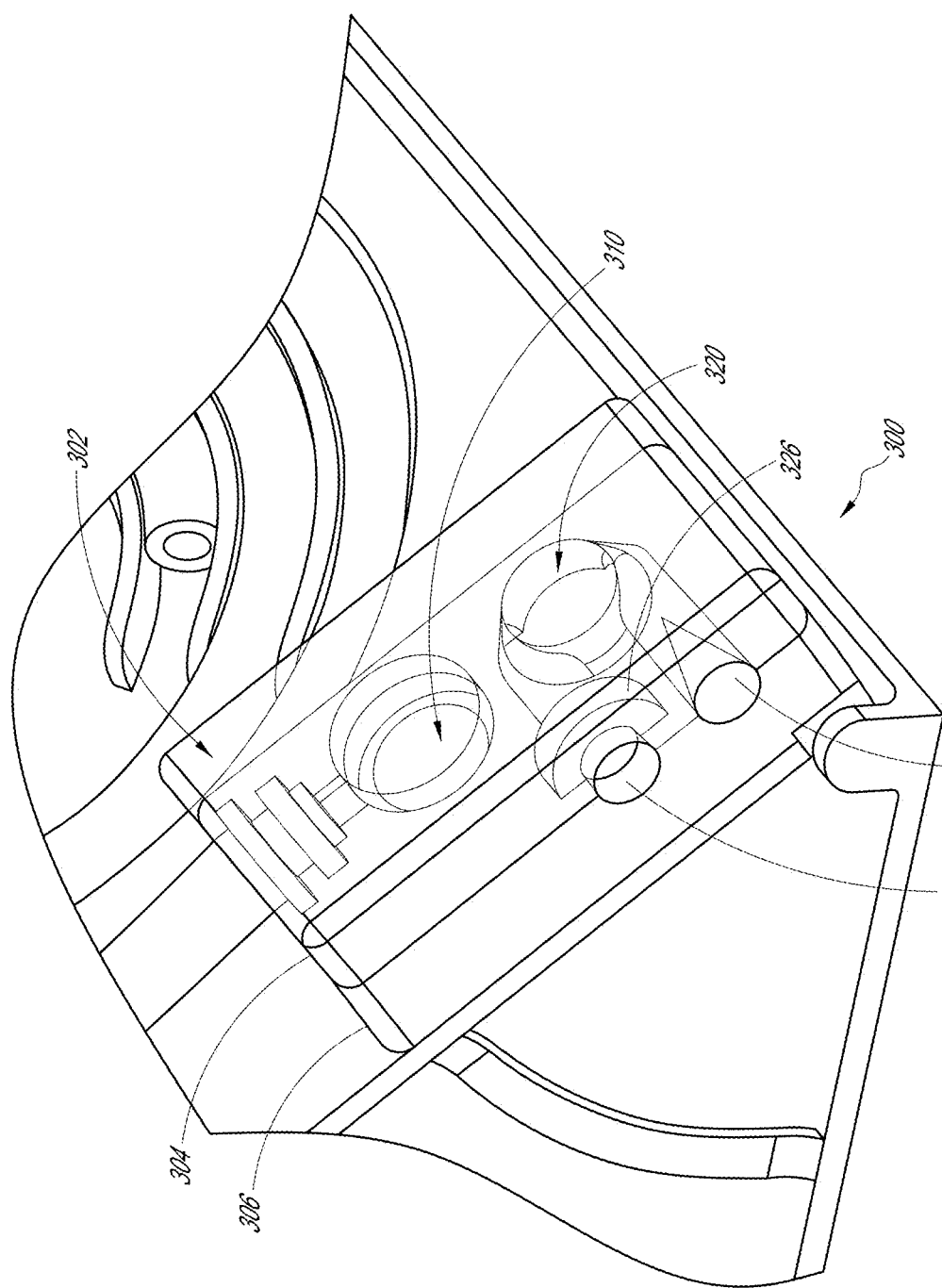
FIG. 4 is a close-up perspective view of the valve assembly of FIG. 2A.

With reference to FIG. 4, the valve assembly 300 can include a case 302, outlet valve 310, inlet valve 320, regulated inlet port 322 and maximum inlet port 324. In the illustrated embodiment, the valve assembly 300 is attached to the upper plate 220 for ease of storage and transport. In some embodiments, the valve assembly 300 can be a separate component connected to the bellows 202 through a tube.

The case 302 encloses the valves and ports of the valve assembly 300. In some embodiments, the case 302 is at least partially transparent so that the interior can be inspected for contamination and proper functioning. For example, the case 302 can be made of a rigid plastic, such as high density polyethylene. In the illustrated embodiment, the top portion 304 of the case 302 is made of a transparent material while the bottom portion 306 is an opaque material. In some embodiments, the top portion 304 can be made of an opaque material while the bottom portion 306 is made of a transparent material. In some embodiments, both the top portion 304 and bottom portion 306 can be made of a transparent material. In some embodiments, both portions 304, 306 can be made of an opaque material.

The valve assembly 300 includes an outlet valve 310 that connects the interior volume of the bellows 202 with the tube 120. In the embodiment illustrated in FIG. 2B, the outlet valve 310 covers the hole 234 in the upper plate 220 and acts as a check valve. The outlet valve 310 allows air to exit the bellows 202, and restricts air and contaminants from entering the bellows 202 through the outlet valve 310. The outlet valve 310 in the illustrated embodiment is a diaphragm valve that pushes the diaphragm into an open configuration when the air pressure in the bellows 202 is greater than the air pressure in the tube 120. In the open configuration, air exits the bellows 202 and is directed through the tube 120. When the pressure in the bellows is less than the pressure in the tube 120, the diaphragm is pressed against the hole 234 to obstruct the air pathway. In some embodiments, the tube 120 can be connected directly to the outlet valve 310. In preferred embodiments, the outlet valve 310 is connected to an adapter that is disposed through the case 302 so that the tube 120 can be connected to the outlet valve 310 without opening the case 302. This is advantageous for quick interchange of tubes 120 for customizing the tubing size for different situations or when replacing damaged tubes 120.

The diaphragm can be made of a conforming material, such as rubber, that is able to form a substantially air tight seal around the hole 234. In other embodiments, the outlet valve 310 can be any of a plurality of different types of valves, such as ball valves, spring valves or butterfly valves, etc. In some embodiments, the outlet valve 310 can be a separate component that is placed in-line between the bellows 202 and the tube 120 instead of through a hole 234 in the upper plate 220.

The valve assembly 300 can also include an inlet valve 320 inside the case 302 that fluidly communicates the interior volume of the bellows 202 with the environment air or a stored air source, such as an oxygen reservoir. The inlet valve 320 allows air to enter the bellows 202, and restricts air and contaminants from exiting the bellows 202 through the inlet valve 320. In the illustrated embodiment, the inlet valve 320 is a diaphragm check valve over another hole 234 in the upper plate 220. The diaphragm valve works similar to the outlet valve 310 described above. When the pressure in the bellows is less than the pressure in the surrounding environment, the diaphragm is in the open configuration and air is allowed to flow into the bellows. When the pressure in the bellows is greater than the pressure in the environment, the diaphragm is pressed against the hole 234 to obstruct the air pathway.

As described with regards to the outlet valve 310, the inlet valve 320 can be any of a plurality of different types of valves, such as ball valves, spring valves or butterfly valves, etc. In some embodiments, the inlet valve 320 can be a separate component that is placed in-line between the bellows 202 and the inlet ports instead of through a hole 234 in the upper plate 220.

The inlet valve 320 can have an inlet port that is open to the environment or connected to other devices, such as an oxygen reservoir or a filter. In the embodiment illustrated in FIG. 3, the inlet valve 320 has a regulated inlet port 322 and a maximum inlet port 324. The regulated inlet port 322 allows air to enter the resuscitator bag 200 at a controlled rate. The maximum inlet port 324 allows air to freely enter the resuscitator bag 200 at a flowrate that is limited by the size of the opening on the maximum inlet port 324. Either the regulated inlet port 322 or the maximum inlet port 324 can be closed with a plug to select the inlet port to be used. In some embodiments, instead of a plug, the inlet valve 320 can have a selector switch that fluidly connects either the regulated inlet port 322 or the maximum inlet port 324 to the inlet valve 320.

The regulated inlet port 322 can be adjustable to change the flowrate through the inlet port. In the illustrated embodiment, the regulated inlet port 322 has a regulator 326 that changes the size of the port opening when the regulator 326 is rotated. In some embodiments, the regulator 326 can be adjusted from the exterior of the valve assembly 300 without opening the case 302. Adjusting the size of the port opening can control the time required for the bellows 202 to inflate. For example, when the regulated inlet port 322 is adjusted to have a small opening, the airflow through the inlet valve 320 is restricted and the time required to fill the bellows 202 takes longer than when the regulated inlet port 322 is adjusted to have a large opening. The ability to customize the inlet flowrate, and thus the time required for the bellows 202 to inflate, is advantageous to control the ventilation rate of the patient, as discussed further below. In some embodiments, the standard fill time for a resuscitator bag 200 can be at least approximately 5 seconds and/or less than or equal to approximately 6 seconds for adults. In some embodiments, the fill time can be at least approximately 3 seconds and/or less than or equal to approximately 7 seconds. In some embodiments for children or small adults, the standard fill time for a resuscitator bag 200 can be at least approximately 3 seconds and/or less than or equal to approximately 4 seconds.

In some embodiments, the regulator 326 can be marked to indicate the fill rate of the bellows. For example, the regulator 326 can be calibrated and labels can be disposed around the circumference of the regulator 326 so that as the regulator 326 is rotated, the fill rate is displayed to the user. In some embodiments, the labels can show the fill rate in seconds. In other embodiments, the labels can display settings, such as "slow," "medium" and "fast."

Biasing Members

The resuscitator bag 200 can include at least one biasing member, such as a spring 204, connected to the upper plate 220 and the lower plate 240 to bias the resuscitator bag 200 in the open configuration. In the illustrated embodiments, the resuscitator bag 200 has two springs 204, one on each side of the resuscitator bag 200. In some embodiments, the spring 204 can be located at the front side of the resuscitator bag 200 or at the rear of the resuscitator bag 200 along the pivoting edge. In some embodiments, the springs can be integrated with the hinges 232, 246 to bias the hinges in the open configuration. Many types of biasing members can be used.

In some embodiments, the biasing force toward the open position can be varied. For example, in some embodiments, the resuscitator bag 200 can have different springs or sets of springs that are selectively used depending on the patient size. A first set of springs can be used for average sized adults and a second set of springs can be used for children or small adults. For example, the second set of springs can be shorter in length than the first set of springs, wherein the second set of springs opens the resuscitator bag 200 less than the first set of springs. The reduced open configuration of the resuscitator bag 200 holds less air volume than when the second set of springs are used, which can be the proper volume for ventilating children and small adults.

The spring 204 can be configured to have a particular spring modulus or stiffness, such that the rate at which the resuscitator bag 200 is opened can be modified for different situations. When the resuscitator bag 200 is opened more rapidly, the ventilation rate can be increased. Accordingly, a stiffer spring can be used when the patient requires rapid ventilation. A spring having a lower spring modulus can be used when the patient needs slow ventilation. Further, the rate at which the resuscitator bag 200 is opened can also be controlled with the regulated inlet port, as described above.

In some embodiments, the springs 204 can be readily detachable from the upper plate 220 and/or lower plate 240 so that the resuscitator bag can be in the compact closed configuration for easier transport or storage. In some embodiments, the upper plate 220 and lower plate 240 can be secured together in the closed configuration, such as with hook and loop fastener straps (e.g., VELCRO® straps). In some embodiments, the resuscitator bag 200 can be held in the closed configuration with a plurality of different types of securing methods, such as hooks, bands, or adhesive tapes.

In some embodiments, the opening force for separating the upper plate 220 and lower plate 240 can be provided by the bellows 202 instead of springs 204. For example, the accordion-like construction of the bellows 202 can be biased in the expanded configuration and provide a spring force to the plates. In some embodiments, the spring force for opening the resuscitator bag 200 can be provided by a combination of the bellows 202 and springs 204.

Indicator

In some embodiments, the upper plate 220 and/or lower plate 240 can have a compression indicator 250 (e.g., a visual indicator) that notifies the user when the resuscitator bag 200 has taken in an appropriate tidal volume of air or is otherwise ready to be compressed. In some embodiments, the compression indicator 250 can include a window 252 through which a strip 254 can be seen. When a predetermined portion of the strip 254 is visible through the window 252, the bag is ready for compression. For example, as the resuscitator bag 200 is opening, the portion of the strip 254 that is visible through the window 252 can provide a first color indicator (e.g., red) or any other indicator to demonstrate that the bag resuscitator bag 200 is not yet full or otherwise not yet ready to dispense air. Once the resuscitator bag 200 has taken in an appropriate tidal volume and is ready for compression, the portion of the strip 254 that is then visible through the window 252 can provide a second color indicator (e.g., green) that is different from the first color indicator.

In the embodiment illustrated in FIG. 5A, a window 252 is disposed on the upper plate 220. The strip 254 is positioned adjacent the window 252 such that a portion of the strip 254 is visible through the window 252. An end of the strip 254 can be secured to the lower plate 240. As the resuscitator bag 200 is opened and closed, the strip 254 slides past the window 252 and different portions of the strip 254 can be visible through the window 252 depending on the configuration of the resuscitator bag 200. For example, in a closed configuration, a first portion 256 of the strip 254 can be visible through the window 252, as illustrated in FIG. 5A. In an open configuration, a second portion 258 of the strip 254 can be visible through the window 252. The user can see when the resuscitator bag 200 is in the open configuration and ready to be depressed by observing the compression indicator 250. The compression indicator 250 advantageously informs the user when to compress the resuscitator bag 200, reducing user error and helping prevent hyperventilation or under-ventilation.

To distinguish between the first portion 256 and second portion 258 of the strip 254, the two portions can be visibly and/or tactilely different. For example, the second portion 258 can have a different color than the first portion 256. In the illustrated embodiment, the second portion 258 is painted black and the first portion 256 is unpainted and has the natural color of the strip 254 material. When the black painted portion of the strip 254 is visible through the window 252, the resuscitator bag 200 is in the open configuration and ready to be compressed. In some embodiments, the second portion 258 can be painted with a bright color that is easily visible. This bright colored embodiment can be used in environments where stealth is not important.

In some embodiments, the strip 254 can have a third portion between the first portion 256 and second portion 258 that indicates when the resuscitator bag 200 is ready to be compressed for smaller patients, such as children or small adults. The third portion can be distinguished from the first portion 256 and second portion 258, such as by a different color or pattern, or any other distinguishing feature discussed herein. In some embodiments, the strip 254 can have more than three portions with distinct colors or other features on the strip 254 to allow further volume customization for ventilation of different sized patients.

In some embodiments, the second portion 258 and/or third portion can have a different tactile sensation. For example, the second portion 258 can be made to have one or more raised surfaces that, when touched by a user, allow the user to discern a pattern or recognizable indicia. Raised surfaces can include ridges, grooves, buttons, dimples, holes, conventional Braille nomenclature, combinations of the foregoing, etc.

In some embodiments, the second portion 258 or third portion can include a material that is visible under infrared or ultraviolet light or a material that allows the identifying element to be viewed in partial or complete darkness using night observation devices or night vision devices, e.g., night vision goggles and/or night vision monoculars. Passive night vision devices (those which pick up any light in the immediate area and amplify it thereby allowing it to be seen) are preferred over active night vision devices (those which project infrared light and produce an image from the light reflected back). The material of the strip 254 can be photoluminescent or it can comprise paints, inks, or dyes of a particular color that facilitate the viewing of the material through night observation devices or night vision devices.

In some embodiments, the second portion 258 or third portion can include attributes that allow it to be visually discerned with the naked eye in low-light or no-light environments. Such attributes may be embodied in materials that include, but are not limited to, photoluminescent materials (e.g., an ink 36 or other material). The photoluminescent materials for use with the present device include, but are not limited to, phosphorescent materials; fluorescent materials; paints, inks, or dyes that emit light when subjected to black light; chemical sources such as phenyl oxalate esters; combinations of the foregoing; and the like. Phosphorescent material is particularly useful for devices that are not intended to be used in situations that require stealth (e.g., civilian paramedic and rescue situations).

Other types of indicators can also be used with this resuscitator bag, including other mechanical indicators or electronic indicators, such as indicators that use position sensors or pressure sensors to detect when the resuscitator bag 200 is in the fully extended configuration or partially extended configuration for smaller patients, and/or indicators that provide an audible sound or a signal light as an indicator of adequate tide volume.

Additional Embodiments

FIGS. 5A-B and 6 illustrate another resuscitator bag according to another embodiment of the resuscitator device. In many ways, this embodiment has similar or identical structures and functions as those disclosed elsewhere herein. Any structure or function in any embodiments herein can be combined with those of other embodiments. In some embodiments, the resuscitator bag 400 can have a central flow line 406 along the pivoting edge of the upper plate 420 and lower plate 440. Attached to the central flow line 406 can be the springs 404, outlet valve 510, inlet valve 520, regulated inlet port 522 and maximum inlet port 524.

The flow line 406 can have a central channel 408 that is in fluid communication with the bellows 402. In the illustrated embodiment, ports 410 connect the bellows 402 to the central channel 408 of the flow line 406. The ports 410 can be connected toward the middle of the flow line 406. The springs 404 can be disposed on the flow line 406 and coupled to the upper plate 420 and lower plate 440 to bias the plates apart. In some embodiments, a spring 404 can be used to bias the upper plate 420 and lower plate 440 apart through connection with the pivoting edge that connects to each respective plate.

In this embodiment, the components of the valve assembly as described above in another embodiment, can be disposed along the central channel 408. An outlet valve 510 can be disposed toward one end of the flow line 406. An inlet valve 520 can be disposed toward the other end of the flow line 406. The ports 410 can be disposed between the outlet valve 510 and inlet valve 520.

An outlet connection port 528 can also be disposed at the end of the flow line 406 on the side of the outlet valve 510. In some embodiments, the outlet connection port 528 can be a quick connect port to allow easy assembly and interchange of tubes to the resuscitator bag 400.

A regulated inlet port 522 and/or maximum inlet port 524 can be disposed at the other end of the flow line 406 near the inlet valve 520. The regulated inlet port 522 and/or maximum inlet port 524 can function similar to as described above. In some embodiments, the regulated inlet port 522 can have a regulator 526 that can be easily adjusted to change the fill time for different patients. In some embodiments, the regulated inlet port 522 and maximum inlet port 524 can be contained in a separate device that can be attached to the inlet valve 520. To resist overly rapid inflation of the resuscitator bag 400 when attached to an oxygen source, an oxygen bag or other reservoir bag with an escape valve can also be attached to the inlet port in fluid communication with the regulated inlet port 522 and/or maximum inlet port 524. The escape valve allows pressure to escape the bag if the pressure in the oxygen or other reservoir bag increases above a preset value.

In some embodiments, an indicator, such as a compression indicator 250, can be positioned in fluid communication with the central flow line 406 and/or mechanically linked with the opening and closing mechanism such as with one or more of the plates or the hinge between them. A window 252 or other viewable portion positioned in or in communication with the flow line 406 can display an indicator, such as a strip 254 as described above. As the upper plate 420 and lower plate 440 are rotated about the pivoting edge, the indicator can provide a signal to a user, such as by configuring strip 254 to change color or pattern and/or to move from one position to another, to indicate when the resuscitator bag 400 has opened sufficiently to provide the desired amount of air upon compression of the bellows 402 of the resuscitator bag 400.

Methods of Use

Some examples of methods of using the bag valve mask disclosed herein will now be described. When medical personnel come upon a patient requiring positive pressure ventilation, the medical personnel can prepare the resuscitator device for use. First, if the resuscitator device is stored in a protective package, the resuscitator device can be removed from the package. In embodiments where the plates 220, 240 of the resuscitator bag 200 are secured together, the securing device can be removed or disconnected. In some embodiments, the appropriate springs 204 can be selected depending on the size of the patient and the springs 204 can be attached to the upper plate 220 and/or lower plate 240, as necessary.

Also, depending on the patient, the regulator 326 on the valve assembly can be adjusted to achieve the correct fill time for the bellows 202, which in turn controls the correct interval between ventilation of the patient. In some embodiments, the interval between ventilation can be at least approximately 5 seconds and/or less than or equal to approximately 5.5 seconds for adults. In some embodiments, the interval can be at least approximately 4 seconds and/or less than or equal to approximately 7 seconds. In some embodiments for children or small adults, the interval can be at least approximately 3 seconds and/or less than or equal to approximately 4 seconds.

In some embodiments, the regulated inlet port 322 and/or maximum inlet port 324 can be connected to an oxygen reservoir. In some embodiments, the ports 322, 324 can be open to the environment to deliver ambient air.

The mask 110 and tube 120 can be removed from the tube holder 226 and placed on the patient, if not already done in an earlier step. The user can then begin the ventilation procedure. In some embodiments, the resuscitator bag 200 can be placed on the ground or other stable surface. Then, the upper plate 220 can be depressed onto the lower plate 240 to ventilate the patient. In some embodiments, the resuscitator bag 200 can be used upside-down, in which case the lower plate 240 can be depressed onto the upper plate 220 to ventilate the patient. In some embodiments, the user can depress the resuscitator bag in a slow, smooth motion. In some embodiments, the springs 204 can provide resistance forces during compression to help prevent the user from depressing the resuscitator bag 200 too quickly.

The user can observe the compression indicator to determine the rate at which the resuscitator bag 200 is to be depressed. After depressing the resuscitator bag 200, the user can release the resuscitator bag 200 to allow the bag to inflate. When the second portion 258 (or third portion in some situations) is visible through the window 252 on the compression indicator 250, the user can depress the resuscitator bag 200 again to ventilate the patient. The patient can be repeatedly ventilated, as necessary. In addition, the user can inspect the bellows 202 and the valve assembly 300 for contamination during ventilation to make sure the operation of the resuscitator bag 200 is not hindered.

Although certain embodiments, features, and examples have been described herein, it will be understood by those skilled in the art that many aspects of the methods and devices illustrated and described in the present disclosure may be differently combined and/or modified to form still further embodiments. For example, any one component of the bag valve mask illustrated and described above can be used alone or with other components without departing from the spirit of the present invention. Additionally, it will be recognized that the methods described herein may be practiced in different sequences, and/or with additional devices as desired. Such alternative embodiments and/or uses of the methods and devices described above and obvious modifications and equivalents thereof are intended to be included within the scope of the present invention. Thus, it is intended that the scope of the present invention should not be limited by the particular embodiments described above, but should be determined only by a fair reading of the claims that follow.

The following is claimed:

1. A resuscitator for providing positive pressure ventilation to patients, the resuscitator comprising:
   an upper plate;
   a lower plate hingedly coupled to the upper plate;
   a bellows disposed between the upper plate and the lower plate;
   at least one biasing member configured to cause relative movement between the upper plate and the lower plate;
   a valve assembly comprising an inlet valve and an outlet valve;
   wherein the valve assembly is in fluid communication with an interior chamber defined by the upper plate, the lower plate and the bellows; and
   a regulator that is operably associated with the valve assembly, wherein the regulator is operable to adjust an inflation rate of the bellows.

2. The resuscitator of claim 1, further comprising at least one inlet port in fluid communication with the resuscitator.

3. The resuscitator of claim 2, wherein the at least one inlet port comprises a first inlet port and a second inlet port, wherein the regulator is coupled to the first inlet port, and wherein the second inlet port allows a free flow of gas.

4. The resuscitator of claim 3, wherein the first and second inlet ports are closable individually.

5. The resuscitator of claim 2, wherein the regulator is coupled to the at least one inlet port.

6. The resuscitator of claim 1, wherein the regulator controls a fill time of the resuscitator.

7. The resuscitator of claim 1, wherein the regulator is adjustable during use of the resuscitator.

8. The resuscitator of claim 1, wherein the upper plate further comprises a cavity for securing a tube and a mask.

9. The resuscitator of claim 1, wherein the at least one biasing member comprises at least one spring.

10. The resuscitator of claim 1, wherein the at least one biasing member is detachable from the resuscitator.

11. The resuscitator of claim 1, wherein the at least one biasing member exerts an expansive force on the upper plate or the lower plate.

12. The resuscitator of claim 1, further comprising a dial functionally linked to the resuscitator, wherein the dial displays a fill time at which the resuscitator moves from a compressed configuration to an expanded configuration, and wherein the fill time corresponds to a ventilation rate for the patient.

13. A resuscitator for providing positive pressure ventilation to patients, the resuscitator comprising:
   an upper plate;
   a lower plate hingedly coupled to the upper plate;
   a bellows disposed between the upper plate and the lower plate;
   at least one biasing member configured to cause relative movement between the upper plate and the lower plate;
   a valve assembly comprising an inlet valve and an outlet valve; and
   a dial functionally linked to the resuscitator, wherein the dial displays a fill time at which the resuscitator moves from a compressed configuration to an expanded configuration, and wherein the displayed fill time corresponds to a ventilation rate for the patient.

14. The resuscitator of claim 13, further comprising a regulator that is operably associated with the valve assembly, wherein the regulator is operable to adjust an inflation rate of the bellows.

15. The resuscitator of claim 13, wherein the at least one biasing member comprises at least one spring.

16. A resuscitator for providing positive pressure ventilation to patients, the resuscitator comprising:
   an upper plate;
   a lower plate hingedly coupled to the upper plate;

a bellows disposed between the upper plate and the lower plate;

at least one biasing member configured to cause relative movement between the upper plate and the lower plate;

a valve assembly comprising an inlet valve and an outlet valve;

a regulator that is operably associated with the valve assembly, wherein the regulator is operable to adjust a flow an inflation rate of a gas the bellows; and a dial functionally linked to the resuscitator, wherein the dial displays a fill time at which the resuscitator moves from a compressed configuration to an expanded configuration, and wherein the fill time corresponds to a ventilation rate for the patient.

17. The resuscitator of claim 16, wherein the at least one biasing member is detachable from the resuscitator.

* * * * *